(12) United States Patent
Neumann

(10) Patent No.: US 11,275,595 B1
(45) Date of Patent: Mar. 15, 2022

(54) SYSTEM AND METHOD FOR PROGRAMMING A MONITORING DEVICE

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/062,769

(22) Filed: Oct. 5, 2020

(51) Int. Cl.
*G06F 9/445* (2018.01)
*G06N 20/00* (2019.01)
*A61B 5/00* (2006.01)

(52) U.S. Cl.
CPC ........... *G06F 9/4451* (2013.01); *G06N 20/00* (2019.01); *A61B 5/00* (2013.01)

(58) Field of Classification Search
CPC .......... G06F 9/4451; G06N 20/00; A61B 5/00
See application file for complete search history.

(56) References Cited

U.S. PATENT DOCUMENTS

| | | | |
|---|---|---|---|
| 7,953,613 B2 | 5/2011 | Gizewski | |
| 8,766,803 B2 | 7/2014 | Bousamra et al. | |
| 10,314,547 B2 | 6/2019 | Miller et al. | |
| 10,360,343 B2 | 7/2019 | Prakash | |
| 10,368,810 B2 | 8/2019 | Quinn et al. | |
| 2003/0036683 A1 | 2/2003 | Kehr | |
| 2006/0047538 A1* | 3/2006 | Condurso | G16H 70/40 705/3 |
| 2007/0232867 A1* | 10/2007 | Hansmann | G16H 40/63 600/300 |
| 2013/0218588 A1 | 8/2013 | Kehr et al. | |
| 2015/0149850 A1* | 5/2015 | Leach | G06F 11/3452 714/751 |
| 2015/0199010 A1* | 7/2015 | Coleman | A61B 5/369 345/156 |

(Continued)

OTHER PUBLICATIONS

Artinian et al, "Pilot study of a Web-based compliance monitoring device for patients with congestive heart failure", [Online], 2003, pp. 226-233, [Retrieved from internet on Oct. 26, 2021], <https://www.sciencedirect.com/science/article/pii/S0147956303000268>(Year: 2003).*

(Continued)

*Primary Examiner* — S. Sough
*Assistant Examiner* — Zengpu Wei
(74) *Attorney, Agent, or Firm* — Caldwell Intellectual Property Law; Keegan Caldwell; Katherine Rubino

(57) ABSTRACT

A system for programming a monitoring device includes a computing device configured to obtain a user datum of a plurality of user datums from a monitoring device, calculate a signal profile as a function of the user datum, identify a scan frequency correlated to the signal profile, wherein identifying further comprises receiving a frequency training set relating at least a first element of a vigor element to at least a first frequency requirement and using a frequency machine learning process, wherein the frequency machine learning process is configured using the signal training set, generate a device scheme as a function of the scan frequency, and program the monitoring device as a function of the device scheme.

18 Claims, 5 Drawing Sheets

(56) References Cited

U.S. PATENT DOCUMENTS

| | | | |
|---|---|---|---|
| 2015/0227837 A1* | 8/2015 | Clifton | G06N 7/005 706/52 |
| 2018/0113982 A1 | 4/2018 | Asthana et al. | |
| 2020/0185100 A1 | 6/2020 | Francois | |
| 2020/0187793 A1* | 6/2020 | Leabman | A61B 5/725 |
| 2020/0195293 A1* | 6/2020 | Leabman | G06F 1/1632 |

OTHER PUBLICATIONS

Uddin et al, "Wearable Sensing Framework for Human Activity Monitoring", [Online], 2015, pp. 21-26, [Retrieved from internet on Oct. 26, 2021], <https://dl.acm.org/doi/pdf/10.1145/2753509.2753513> (Year: 2015).*
https://www.mdpi.com/2079-4991/9/6/813.
https://www.himss.org/resources/wearable-technology-applications-healthcare-literature-review.
http://www.selectsmart.com/fitnesstracker/.

* cited by examiner

SYSTEM AND METHOD FOR PROGRAMMING A MONITORING DEVICE

FIELD OF THE INVENTION

The present invention generally relates to the field of artificial intelligence. In particular, the present invention is directed to a system and method for programming a monitoring device.

BACKGROUND

Monitoring devices are constantly being upgraded and altered due to software updates, mechanical updates, and consumer preference, which is preventing efficient customization as each new iteration restarts the relationship between the consumer and the monitoring device. This lack of consistency reduces the monitoring device capability and results in consumer frustration.

SUMMARY OF THE DISCLOSURE

In an aspect, a system of programming a monitoring device includes a computing device, the computing device further configured to, obtain a user datum of a plurality of user datums from a monitoring device, calculate a signal profile as a function of the user datum, wherein calculating further comprises receiving a signal training set relating a monitoring element to a vigor adjustment outcome and using a signal machine-learning process, wherein the signal machine learning process is configured using the signal training set, identify a scan frequency correlated to the signal profile, wherein identifying further comprises receiving a frequency training set relating at least a first element of a vigor element to at least a first frequency requirement and using a frequency machine learning process, wherein the frequency machine learning process is configured using the signal training set, generate a device scheme as a function of the scan frequency, and program the monitoring device as a function of the device scheme.

In another aspect, a method of programming a monitoring device includes obtaining, by a computing device, a user datum of a plurality of user datums from a monitoring device, calculating, by a computing device, a signal profile as a function of the user datum, wherein calculating further comprises receiving a signal training set relating a monitoring element to a vigor adjustment outcome and using a signal machine-learning process, wherein the signal machine learning process is configured using the signal training set, identifying, by a computing device, a scan frequency correlated to the signal profile, wherein identifying further comprises receiving a frequency training set relating at least a first element of a vigor element to at least a first frequency requirement and using a frequency machine learning process, wherein the frequency machine learning process is configured using the signal training set, generating, by a computing device, a device scheme as a function of the scan frequency, and programing, by a computing device, the monitoring device as a function of the device scheme.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for programming a monitoring device. In an embodiment, this system programs a monitoring device as a function of a user datum. Aspects of the present disclosure can be used to program a monitoring device that at least alters the monitoring as a function of the user datums detected by the monitoring device. This is so, at least in part, because the system obtains a user datum from a monitoring device and generates, via a machine-learning process, an efficient monitoring strategy for the user. Exemplary embodiments illustrating aspects of the present disclosure are described below in the context of several specific examples.

Figure 1:
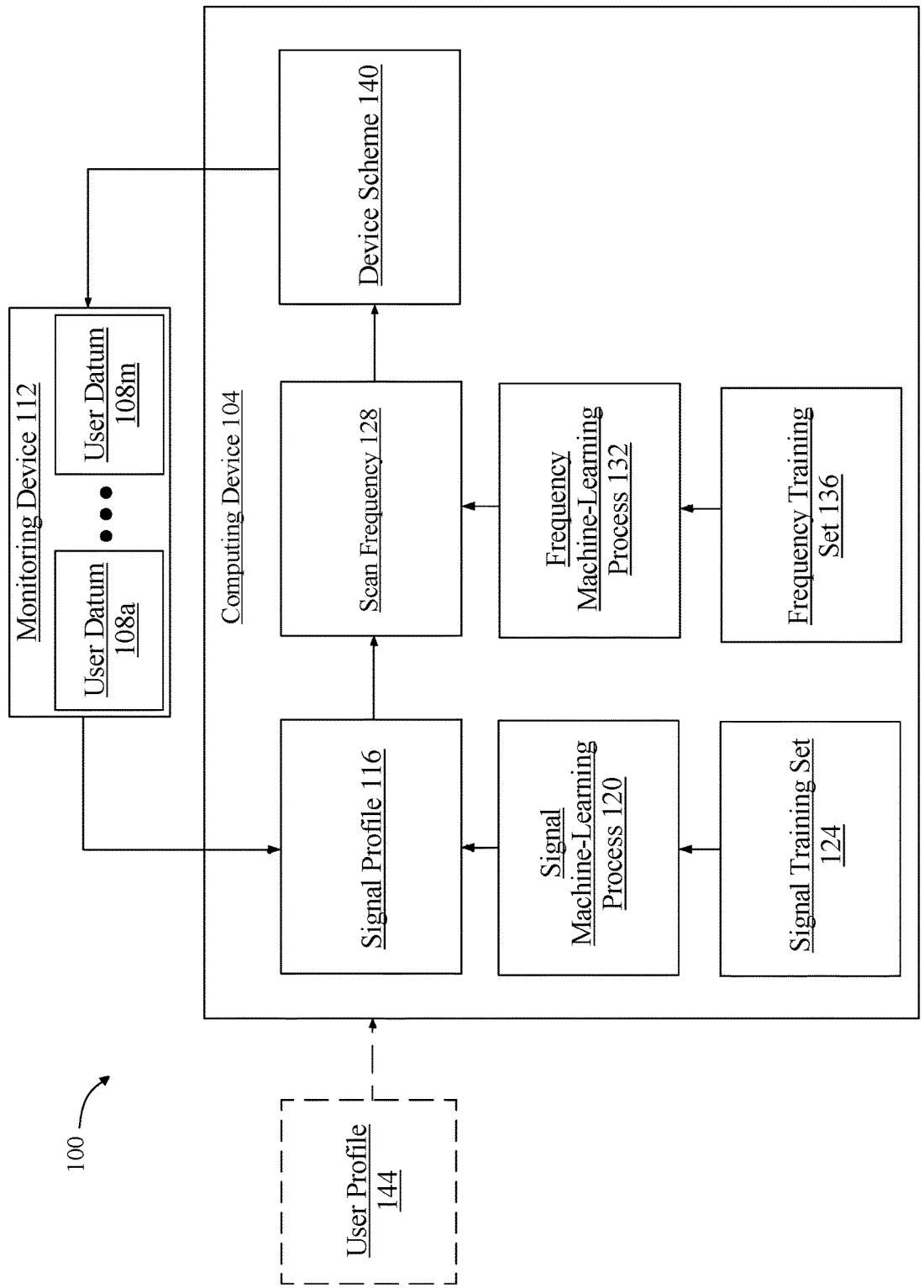
FIG. 1 is a block diagram illustrating an exemplary embodiment of a system for programming a monitoring device.

Referring now to FIG. 1, an exemplary embodiment of a system 100 for programming a monitoring device is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains, a user datum 108a of a plurality of user datums 108a-m from a monitoring device 112. As used in this disclosure a "user datum" is a sign, symptom, element, or quality that relates to a user. For instance, a user datum may include, without limitation, heart rate, calories burned, steps walked, blood pressure, biochemicals detected, time spent exercising, seizures, physical strain, or the like thereof. As a further non-limiting example, user datum may include mood quality, anxiety levels, sleep quality, or the like thereof. As used in this disclosure "monitoring device" is an electronic device that is worn on the person of a user, such as without limitation close to and/or on the surface of the skin, wherein the device can detect, analyze, and transmit information concerning a body signal such as a vital sign, and/or ambient datum, wherein allowing immediate biofeedback to be sent to the user wearing the device. Monitoring device 112 may include, without limitation, any device that further collects, stores, and analyzes data associated with user datums. Monitoring device 112 my consist of, without limitation, near-body electronics, on-body electronics, in-body electronics, electronic textiles, smart watches, smart glasses, smart clothing, fitness trackers, body sensors, wearable cameras, head-mounted displays, body worn cameras, Bluetooth headsets, wristbands, smart garments, chest straps, sports watches, fitness monitors, and the like thereof. Monitoring device 112 may include, without limitation, earphones, earbuds, headsets, bras, suits, jackets, trousers, shirts, pants, socks, bracelets, necklaces, brooches, rings, jewelry, AR HMDs, VR HMDs, exoskeletons, location trackers, and gesture control wearables.

With continued reference to FIG. 1, computing device 104 calculates a signal profile 116 as a function of user datum 108. As used in this disclosure a "signal profile" is a value associated with the effect of the user datum on a user. Signal profile 116 may be comprised of a user vigor status. As used in this disclosure a "user vigor status" is a qualitative measure of a user health. User vigor status may include, without limitation, a user condition, a user fitness status, a user wellness goal, a user medical goal, or the like thereof. As used in this disclosure a "user condition" is a list or collection of current or potential ailments and/or diseases, and/or precursor states to such ailments and/or diseases, including but not limited to physical, spiritual, and/or psychological ailments and/or diseases correlating to any resulting impact on the user. In an embodiment a physical ailment or disease may include, without limitation, Influenza, Rhinovirus, Obesity, COVID-19, EEE, CRE, Ebola, Enterovirus D68, Influenza, Hantavirus, Hepatitis A, Hepatitis A, HIV/AIDS, Diabetes (Type I or Type II), Multiple Sclerosis, Chron's Disease, Colitis, Lupus, Rheumatoid Arthritis, Allergies, Asthma, Relapsing Polychondritis, Scleroderma, Liver Disease, Heart Disease, Cancer, and the like thereof. In an embodiment a spiritual ailment or disease may include, without limitation, religious conflicts, chakra blockages, existential crisis, or the like thereof. In an embodiment a psychological ailment or disease may include, without limitation, Alzheimer's, Parkinson's, alcohol or substance abuse disorder, anxiety disorder, ADD, ADHD, bipolar disorder, depression, eating disorder, obsessive-compulsive disorder, opioid use disorder, PTSD, schizophrenia, depersonalization disorder, dissociative amnesia and/or fatigue, anorexia, bulimia, sleep disorders, wake disorders, paraphilic disorders, sexual disorders, child mental disorders, personality disorders, gender dysphoria, depression, and the like thereof. As used in this disclosure a "user fitness status" is an enumeration vector relating a user fitness to a fitness capability. For example, and without limitation, a user fitness status may indicate a user to have a low fitness status, wherein a low fitness status indicates the user to be below average for fitness levels. As used in this disclosure a "user wellness goal" is a set value or metric that a user would like to achieve relating to the user's wellness. For example, and without limitation, a user wellness goal may include increased sleep, enhanced meditation, increase positivity, or the like thereof. As used in this disclosure a "user medical goal" is a set value or metric that a user and/or physician would like the user to achieve to increase overall medical health. For example, and without limitation, a user medical goal may include decrease LDL, lower blood pressure, reduced heart rate, increased lung capacity, increased metabolic rate, or the like thereof. Signal profile 116 may be comprised of a vector enumeration relating to a user datum. As used in this disclosure a "vector enumeration" is a measurable value generated as a function of either a quantitative or qualitative user datum.

For example, and without limitation, a vector enumeration may generate a value of 20 for a user datum related to high blood pressure values. As a further non-limiting example a value of 100 may be generated as a function of a user datum related to a myocardial infarction. Signal profile 116 may utilize vector enumeration to calculate the value of the user element in relation to a signal of a user condition, a frequency of the user datum occurrence and/or the identification of a secondary user datum. For example, and without limitation, a user datum of heart rate may be detected such that an arrythmia is found, wherein a signal profile relating to arrythmia may be calculated as a value of 50. As a further non-limiting example signal profile 116 may be calculated as a function of a frequency of the user datum, wherein a high blood glucose value may detected more than 5 times within a given time period such that the signal profile may calculate a value of 50 for diabetes.

With continued reference to FIG. 1, computing device may calculate signal profile 116 as a function of a signal machine-learning process 120. As used in this disclosure "signal machine-learning process" is a machine learning process that automatedly uses training data and/or a training set to generate an algorithm that will be performed by a computing device and/or module to produce outputs given data provided as inputs; this is in contrast to a non-machine learning software program where the commands to be executed are determined in advance by a user and written in a programming language. Signal machine-learning process 120 may consist of any supervised, unsupervised, or reinforcement machine-learning process that computing system 104 may or may not use in the determination of signal profile 116. Signal machine-learning process 120 may include, without limitation, machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, signal machine-learning process 120 may be calculated as a function of a signal training set 124. As used in this disclosure "signal training set" is a training set that correlates a monitoring element to a vigor adjustment outcome. As used in this disclosure a "monitoring element" is an element relating to one or more human physiological statuses, wherein human physiological statuses may include heartbeat, blood pressure, body temperature, electrocardiograms, arrhythmias, cancerous indicators, body fat composition, or the like thereof. As a non-limiting example, monitoring elements may include data collected from using one or more pressure sensors, humidity sensors, position sensors, piezo film sensors, force sensors, temperature sensors, optical sensors, or the like thereof. As a further non-limiting example monitoring elements may include data collected from using X-ray absorptiometry, hydrostatic weighing, air displacement plethysmography, bioelectrical impedance analysis, bioimpedance spectroscopy, electrical impedance myograph, 3-D scanners, and multi-compartment models. As used in this disclosure a "vigor adjustment outcome" is an effect, impact, consequence, result, reaction, or the like thereof that may result as a function of a monitoring element. For example, and without limitation, a vigor adjustment outcome of pneumonia may be related to the monitoring elements of decreased lung capacity, fever, shortness of breath, coughing, or the like thereof. A vigor adjustment outcome may include a monitoring element wherein the vigor adjustment outcome is positive, such as, and without limitation, body fat percentage loss related to increased heart stamina and/or efficiency. A vigor adjustment outcome may include a monitoring element wherein the vigor adjustment outcome is negative, such as, and without limitation, heart arrythmias related to congenital heart disease. Additionally or alternatively signal machine learning process 120 may be generated as a function of a classifier, wherein the classifier may receive a monitoring device element of a plurality of monitoring elements and output one or more vigor adjustment outcomes that are related to at least one or more monitoring elements. As used in this disclosure a "classifier" is a machine-learning model, such as a mathematical model, neural net, or program generated by a machine learning algorithm known as a "classification algorithm," as described below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a process whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. For example, and without limitation, a classifier may receive an input of a monitoring element associated with increased pressure on the epidermal layer of a user, wherein a vigor adjustment outcome may identify increased blood flow, swelling, and/or infection.

Still referring to FIG. 1, computing device 104 may generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 identifies a scan frequency 128 correlated to signal profile 116. As used in this disclosure a "scan frequency" is a number of scans that are conducted over a given period of time, wherein a period of time is comprised of milliseconds, seconds, minutes, hours, days, weeks, months, years, and the like thereof. Scan frequency 128 may be comprised of the number of scans required to monitor the user datum. For example, and without limitation, a scan frequency of 10 scans may be identified for a user datum of elevated anxiety. Scan frequency 128 may be comprised of a number of scans necessary to at least monitor a user condition in a time period. As used in this disclosure a "time period" is a given measure of time intervals. For example, a time period may include milliseconds, seconds, minutes, hours, days, weeks, months, years, or the like thereof. For example, and without limitation, a scan frequency of 30 scans per hour may be required for the user datum pertaining to blood clots.

Still referring to FIG. 1, computing device 104 identifies scan frequency through the use of a frequency machine-learning process 132. As used in this disclosure "frequency machine-learning process" is a machine learning process that automatedly uses training data and/or a training set to generate an algorithm that will be performed by a computing device and/or module to produce outputs given data provided as inputs; this is in contrast to a non-machine learning software program where the commands to be executed are determined in advance by a user and written in a programming language. Frequency machine-learning process 132 may consist of any supervised, unsupervised, or reinforcement machine-learning process that computing system 104 may or may not use in the determination of scan frequency 128. Frequency machine-learning process 132 may include, without limitation, machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, frequency machine-learning process 132 may be generated as a function of a frequency training set 136. As used in this disclosure "frequency training set" is a training set that correlates at least a first element of a vigor element to at least a first frequency requirement. As used in this disclosure a "vigor element" is an element relating to one or more human physiological, psychological, or spiritual states, wherein a physiological state relates to one or more metabolic and/or biological processes, a psychological state relates to one or more neurologic and/or emotional processes, and a spiritual state relates to one or more religious and/or existential elements. As a non-limiting example, vigor elements may include lung capacity, edema pressure, neural transmission, mood quality, religious quarrel, and/or religious hopelessness. As used in this disclosure a "frequency requirement" is a value denoting a necessary and/or useful frequency of monitoring for a given user datum. For example, and without limitation, a frequency requirement of pneumonia may be 40 scans per day due to the decreased lung capacity, fever, shortness of breath, coughing, or the like thereof. Additionally or alternatively frequency machine learning process 132 may be generated as a function of a classifier, described above, wherein the classifier may receive a vigor element of a plurality of vigor elements and output one or more frequency requirements in monitoring the vigor element. For example, and without limitation, a classifier may receive an input of a vigor element associated with macular degeneration, wherein a frequency requirement outcome may be 10 scans per minute to ensure effective monitoring.

Still referring to FIG. 1, computing device 104 generates a device scheme 140 as a function of scan frequency 128. As used in this disclosure a "device scheme" is a schedule of scans that is generated as a result of a given scan frequency and a given time period that may be entered into a device such that the device monitors the user effectively. For example, and without limitation, a device scheme may generate a scan every 8.5 minutes for a scan frequency of 210 scans over 30 hours. Computing device 104 may generate device scheme 140 by receiving scan frequency 128 relating to user datum 108. Computing device 104 may determine a given time period, as described above to include milliseconds, seconds, minutes, hours, days, weeks, months, years, and the like thereof, to fulfill the frequency requirement, as described above. As used in this disclosure a "scan frequency" is a required number of scans of a monitoring device to at least monitor a given user datum. Computing device 104 may generate a device scheme as a function of the scan frequency and time period. For example, and without limitation, a given scan frequency may include 40 scans to effectively monitor a microvascular cranial nerve palsy and the given time period is daily, wherein the device schedule may be generated to determine a scan needs to be performed every 36 minutes. In an embodiment, and without limitation, computing device 104 may generate device scheme 140 by outputting a first device scheme as a function of a first scan frequency relating to a first signal profile, wherein the first signal profile relates to a first user datum recorded by a monitoring device. For example, and without limitation, a device scheme of scanning every 8 hours and 24 minutes may be generated as a function of a scan frequency of 20 scans over a 1-week time period.

Still referring to FIG. 1, computing device 104 may identify a second scan frequency as a function of user profile 144 and first signal profile. A "user profile" as used in this disclosure is a characteristic uniquely belonging to a human subject. A user profile may include, without limitation, particular traits, qualities, behaviors, and/or habits relating to a user. User profile may be comprised of a medical record and/or user demographic, wherein a user demographic relates one or more elements of age, sex, gender, weight, height, geolocation, and/or ethnicity. User profile 144 may be received as a function of physician input, self-report, familial report, or the like thereof. For example, and without limitation, a user's physician may input to computing device 104 that a user profile indicates high blood pressure and a high LDL value. As a further non-limiting example a user may self-report a user profile of anxiety to computing device 104. For example, and without limitation, a first signal profile may indicate a presence of a heart arrythmia while a user profile may indicate the presence of congenital heart failure, wherein a second scan frequency may be generated as a function of both arrhythmia and congenital heart failure. Computing device 104 may generate a second device scheme as a function of the second scan frequency, wherein the second device scheme incorporates both the user profile and the first signal profile. For example, and without limitation, a second device scheme of scanning every 5 minutes may be generated as a function of a scan frequency of 12 scans per hour, wherein the scan frequency was identified as a function of a combination between a user profile of COVID-19 and a first scan frequency of 10 scans per hour. Additionally or alternatively, computing device 104 may be configured to generate second device scheme as a function of second scan frequency relating to a second signal profile. The second signal profile may be calculated as a function of a second user datum 108$m$. For example, and without limitation, a first user datum of jaundice may be obtained by a monitoring device, wherein a second user datum of fever is then obtained by monitoring device 112. Computing device 104 may then calculate the second signal profile, wherein calculating results in identifying second scan frequency and second device scheme.

With continued reference to FIG. 1, computing device 104 is configured to program monitoring device 112 as a function of device scheme 140. Monitoring device 112 is programmed by computing device such that the user datum and/or user profile can be effectively monitored according to device scheme 140. Computing device 104 may receive a second device scheme, wherein the generation of a second device scheme is described above. Computing device 104 may identify a first device scheme on monitoring device 112. For example, and without limitation, a previous device scheme may include the monitoring device providing a scan 36 times over a 6-hour time period. Computing device 104 may program monitoring device 112 as a function of the second device scheme, wherein the second device scheme modifies the monitoring of the first device scheme. For example, and without limitation, a first device scheme may have monitoring device 112 conducting a scan every 3 minutes over a 24 hour time period, while a second device scheme may have monitoring device 112 conducting a scan every 2 minutes over a 24 hour scan to increase the overall number of scans for a given user profile and/or user datum.

Figure 2:
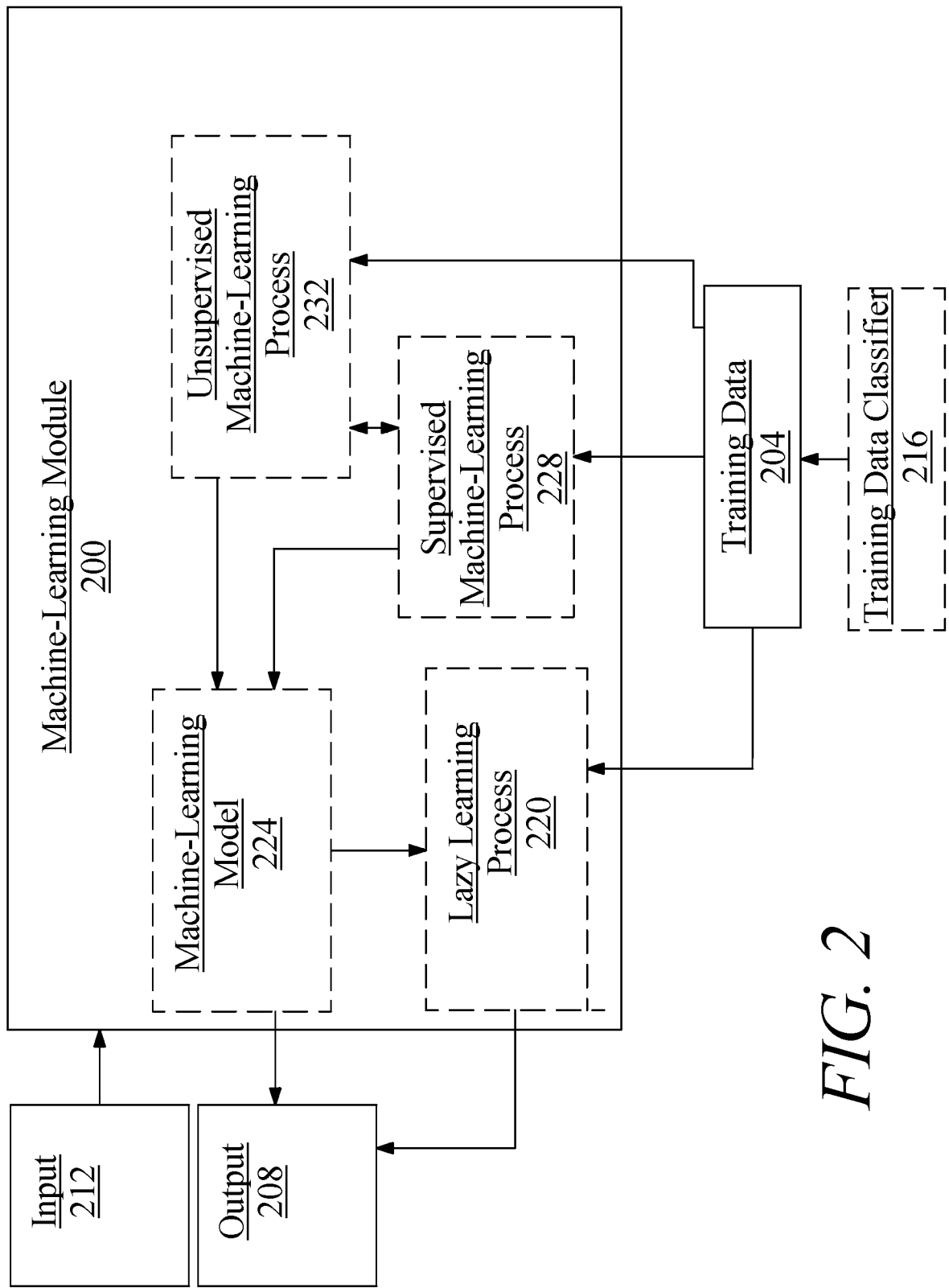
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example a frequency training set may be used as an input and a scan frequency output may be generated as a function of the frequency machine learning process.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to scan frequencies wherein a classifier may characterize a sub-population of scan frequencies as a function of the type of scan frequency, wherein a type of scan frequency may relate to the location of the monitoring device.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a frequency training set as described above as inputs, scan frequencies as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
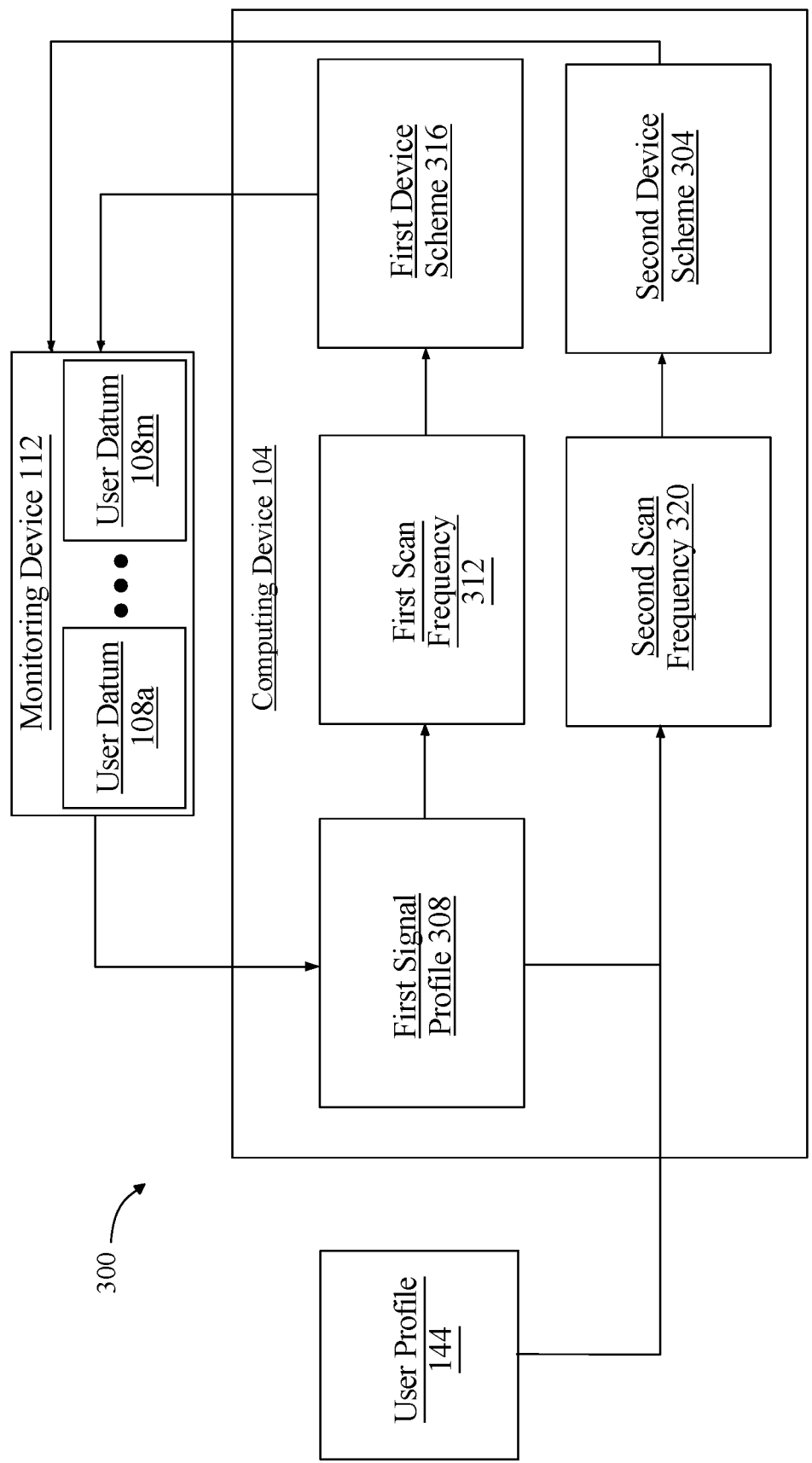
FIG. 3 is a block diagram of an exemplary embodiment of user profile generating a second device scheme according to an embodiment of the invention.

Now referring to FIG. 3, an exemplary embodiment of 300 of user profile 144 generating a second device scheme 304 according to an embodiment of the invention. In an embodiment, computing device 104 may obtain user datum 108*a-m* and calculate a first signal profile 308 as a function of user datum 108*a*. For example, and without limitation, a first user datum of loss of sleep quality may calculate s first signal profile of 20 for sleep apnea. Computing device 104 may identify a first scan frequency 312 as a function of first signal profile 308. For example, and without limitation a scan frequency of 40 scans per month may be identified for a fitness goal of increasing 10 pounds of muscle mass in a 6-month period. Computing device 104 may generate a first device scheme 316 as a function of first scan frequency 312 and program monitoring device 112 as a function of first device scheme 316. As a non-limiting example a device scheme of conducting a scan every 18 minutes to monitor a medical goal of decreasing LDL concentration in a user's circulatory system may be sent to monitoring device 112 such that monitoring device 112 is programmed for those scans. Computing device 104 may identify a second scan frequency 320 as a function of user profile 144 and first signal profile. As a non-limiting example user profile 144 a first signal profile 308 may indicate a presence of chakra blockage while user profile 144 may indicate the presence of religious hopelessness, wherein second scan frequency 320 may be generated as a function of both chakra blockage and religious hopelessness. Computing device 104 may generate second device scheme 304 as a function second scan frequency 320 and program monitoring device 112 as a function of second device scheme 304. For example, and without limitation, a second device scheme of 30 scans per hour may be generated as a function of a combination between a user profile of Influenza and a first scan frequency of 20 scans per hour. Additionally or alternatively, computing device 104 may be configured to generate second device scheme 304 as a function of second scan frequency 320 relating to a second signal profile. The second signal profile may be calculated as a function of a second user datum 108*m*. For example, and without limitation, a first user datum of anxiety has resulted in a device scheme of monitoring every 30 minutes for 30 days followed by a second user datum of increase elevated epinephrine, wherein second device scheme 304 may be altered to scan every 5 minutes for 116 days.

Figure 4:
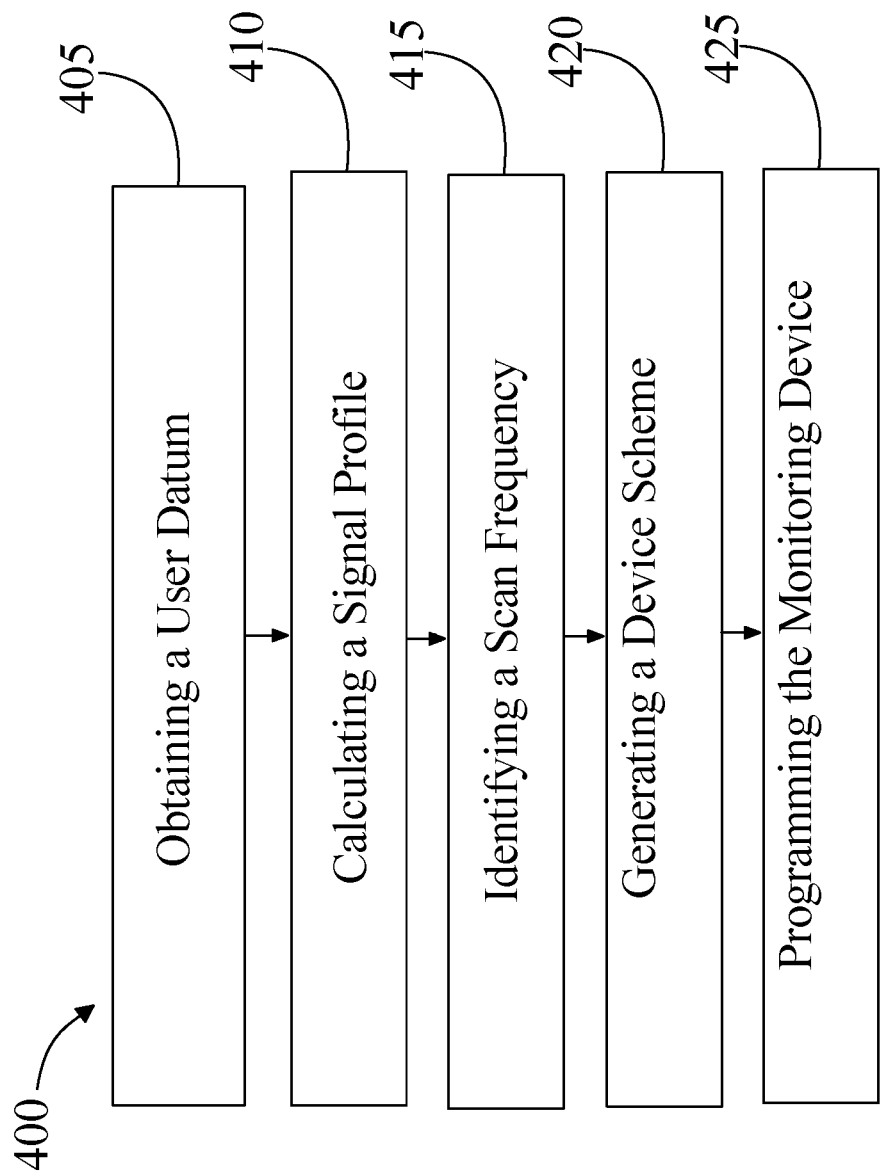
FIG. 4 is a process flow diagram illustrating an exemplary embodiment of a method for programming a monitoring device.

Now Referring to FIG. 4, an exemplary embodiment of a method 400 of programming a monitoring device, at step 405 a computing device obtains a user datum 108 from a monitoring device 112. User datum 108 includes any of the user datum 108 as described above in reference to FIGS. 1-3. User datum may include a sign, symptom, element, or quality that relates to a user. For instance, a user datum may include, without limitation, neurologic function, sleep cycle, linguistic quality, heart rate, calories burned, steps walked, blood pressure, mood quality, anxiety levels, or the like thereof. Monitoring device 112 includes any of the monitoring device 112 as described above in reference to FIGS. 1-3. Monitoring device 112 may include, without limitation, any smart electronic device that is worn close to and/or on the surface of the skin, wherein the device can detect, analyze, and transmit information concerning a body signal such as a vital sign, and/or ambient datum, wherein allowing immediate biofeedback to be sent to the user wearing the device. Monitoring device 112 may include devices such as smart watches, head mounts, electronic textiles, smart glasses, smart clothing, smart jewelry, and the like thereof. For example, and without limitation, a monitoring device of a smart watch containing an optical sensor may provide a user datum of heart rate to computing device 104.

With continued reference to FIG. 4, at step 410, computing device calculates, a signal profile 116 as a function of user datum 108. Signal profile 116 includes any of the signal profile as described above in reference to FIGS. 1-3. Signal profile may be calculated as a function of a signal of a user condition, a frequency of the user datum occurrence, the identification of a secondary user datum that differs from a previous signal profile. For instance and without limitation, signal profile may calculate a value of 75 for influenza due to the user datums of sneezing, coughing, shortness of breath, and decreased $O_2$ saturation levels. Computing device 104 may calculate signal profile 116 as a function of one or more machine-learning processes as described above in reference to FIGS. 1-3. Computing device 104 may calculate signal profile 116 as a function of a signal machine-learning process 120. Signal machine-learning process 120 includes any of the signal machine-learning process 120 as described above in reference to FIGS. 1-3. For instance, and without limitation, signal machine-learning process 120 may include a supervised machine-learning process or an unsupervised machine-learning process. Signal machine learning process 120 may include a classification process, such as for example naïve Bayes, k-nearest neighbor, decision tree, and/or random forest. Classification processes include any of the classification processes as described above in reference to FIGS. 1-3. Signal machine-learning process 120 may be configured using a signal training set 124. Signal training set 124 includes any of the signal training set 124 as described above in reference to FIGS. 1-3. Signal training set 124 may include, without limitation, a monitoring element correlated to a vigor adjustment outcome, wherein a monitoring element relates to one or more human physiological statuses and a vigor adjustment outcome is any effect, impact, consequence, result, or reaction that may result from that monitoring element.

Still referring to FIG. 4, at step 415, computing device 104 identifies a scan frequency 128 correlated to signal profile 116. Scan frequency 128 includes any of the scan frequency 128 as described above in reference to FIGS. 1-3. Scan frequency 128 may include a number of scans that are conducted over a given period of time, wherein a period of time is comprised of milliseconds, seconds, minutes, hours, days, weeks, months, years, and the like thereof. For example, and without limitation, a scan frequency for weight loss may include 12 scans per day. Scan frequency 128 may be comprised of the number of scans required to monitor the user datum. For example and without limitation, 40 scans may be required to monitor the user datum of premature ventricular contractions. Scan frequency 128 may be comprised of a number of scans necessary to at least monitor a user condition in a time period. For example, and without limitation a number of 5 scans may be necessary to monitor a user condition of a fever over a 24-hour time period. Computing device 104 may calculate scan frequency 128 as a function of one or more machine-learning processes as described above in reference to FIGS. 1-3. Computing device 104 may calculate scan frequency 128 as a function of a frequency machine-learning process 132. Frequency machine-learning process 132 includes any of the frequency machine-learning process 132 as described above in reference to FIGS. 1-3. For instance, and without limitation, frequency machine-learning process 132 may include a supervised machine-learning process or an unsupervised machine-learning process. Frequency machine learning process 132 may include a classification process, such as for example naïve Bayes, k-nearest neighbor, decision tree, and/or random forest. Classification processes include any of the classification processes as described above in reference to FIGS. 1-3. Frequency machine-learning process 132 may be configured using a frequency training set 136. Frequency training set 136 includes any of the frequency training set 136 as described above in reference to FIGS. 1-3. Frequency training set 136 may include, without limitation, at least a first element of a vigor element to at least a first frequency requirement, wherein a vigor element is an element relating to one or more human physiological, psychological, or spiritual states and a frequency requirement may consist of a value denoting a necessary frequency of monitoring for a given user profile and/or user datum. For example, and without limitation, frequency training set 136 may correlate rhabdomyolysis with a frequency requirement of 10 scans per second.

Still referring to FIG. 4, at step 420, computing device 104 generates a device scheme 140 as a function of scan frequency 128. Device scheme 140 includes and of the device scheme 140 as described above in reference to FIGS. 1-3. Device scheme may include a schedule that may or may not be generated as a function of a given scan frequency and a given time period that may be entered into a device such that the device monitors the user effectively. Computing device 104 may generate a second device scheme 304 as a function of user profile 144. Computing device 104 may output a first device scheme 316 as a function of a first scan frequency 312, wherein first scan frequency 312 is identified as a function of a first signal profile 308. Computing device 104 may then identify a second scan frequency 320 as a function of user profile 144 and first signal profile 308. Computing device may then generate a second device scheme 304 as a function of second scan frequency 320. For example, and without limitation, a first device scheme of a scan every 20 minutes over a 4 day time period may be altered to a second device scheme of a scan every 5 minutes over a 12 day time period due to the user profile input of previous myocardial infarction. Additionally or alternatively, computing device 104 generate second device scheme 304 as a function of a second scan frequency 312 relating to a second signal profile. The second signal profile may be calculated as a function of a second user datum 108*m*. For example, and without limitation, a first user datum of high blood pressure may be obtained by a monitoring device, wherein a second user datum of myocardial infarction is then obtained by monitoring device 112. Computing device 104 may then calculate the second signal profile, wherein calculating results in identifying second scan frequency 320 and second device scheme 304.

Still referring to FIG. 4, at step 425, computing device 104 programs monitoring device 112 as a function of device scheme 140. Computing device 104 programs monitoring device 112 such that the user datum and/or user profile can be effectively monitored according to device scheme 140. Computing device 104 may receive second device scheme 304, wherein the generation of a second device scheme is described above, identify first device scheme 140 on monitoring device 112, and program monitoring device 112 as a function of second device scheme 304, wherein second device scheme 304 modifies first device scheme 140. For example, and without limitation, a first device scheme may have monitoring device 112 conducting a scan every 3 minutes over a 24 hour time period, while a second device scheme may have monitoring device 112 conducting a scan every 2 minutes over a 24 hour scan to increase the overall number of scans for a given user profile and/or user datum.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
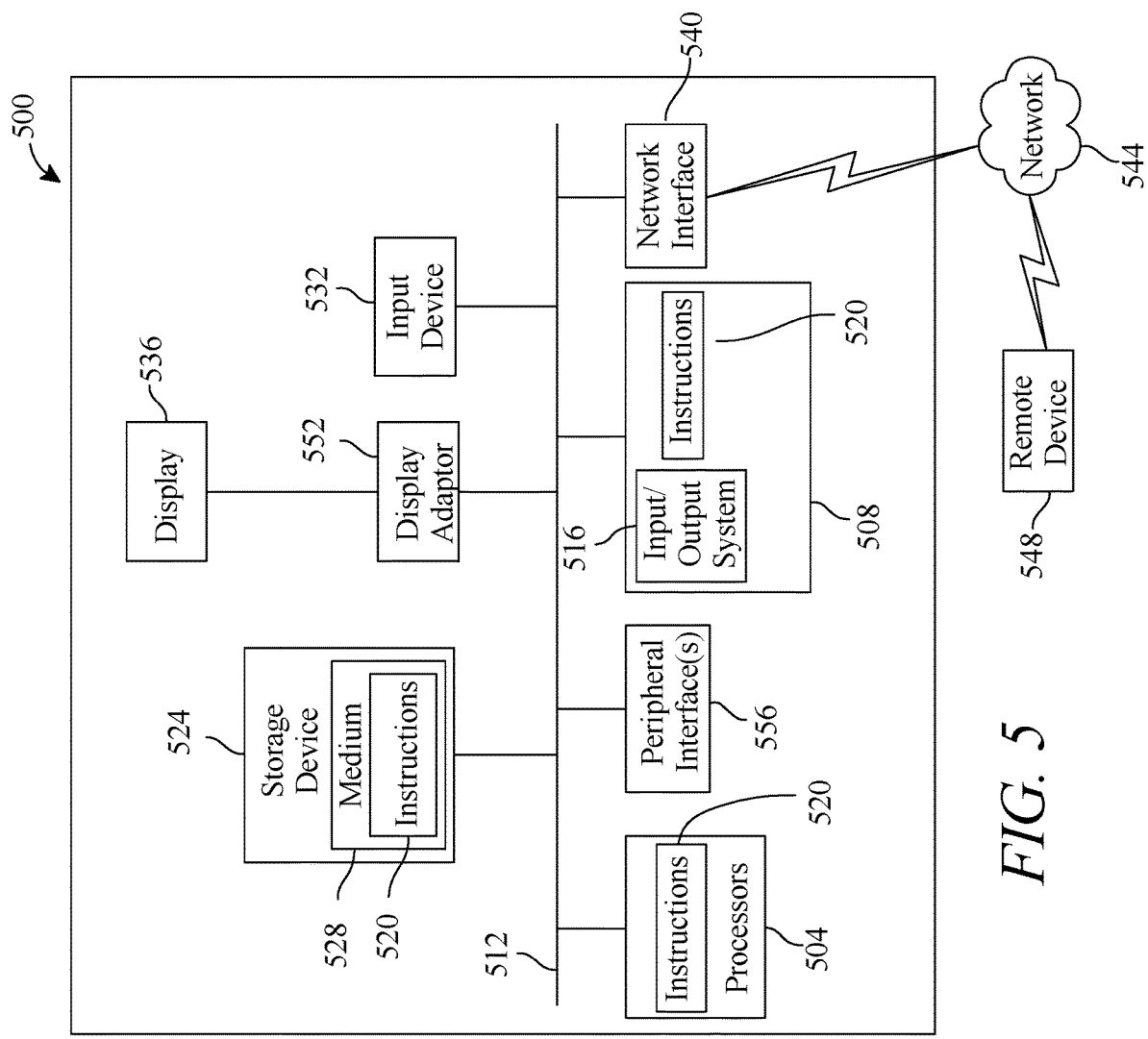
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for programming a monitoring device, the system comprising:
   a computing device, the computing device configured to:
   obtain, from a monitoring device, a user datum of a plurality of user datum;
   calculate a signal profile as a function of the user datum, wherein calculating the signal profile further comprises:
      receiving a signal training set, wherein the signal training set correlates a monitoring element and a vigor adjustment;
      configuring a signal machine-learning process as a function of the signal training set; and
      calculating the signal profile as a function of the signal machine learning process and the user datum;
   identify a scan frequency as a function of the signal profile, wherein identifying further comprises:
      receiving a frequency training set, wherein the frequency training set correlates at least a first vigor element and at least a first frequency requirement; and
      training a frequency machine-learning process as a function of the frequency training set; and
      identifying the scan frequency as a function of the signal profile and the frequency machine-learning process;
   generate, automatically, a device scheme as a function of the scan frequency; and
   program the monitoring device as a function of the device scheme.

2. The system of claim 1, wherein the signal profile further comprises a user vigor status.

3. The system of claim 1, wherein the signal profile comprises a vector enumeration relating to the user datum.

4. The system of claim 1, wherein the scan frequency comprises a number of scans required to monitor the user datum.

5. The system of claim 1, wherein the scan frequency further comprises a number of scans to at least monitor a user condition in a time period.

6. The system of claim 1, wherein generating the device scheme further comprises:
   receiving a scan frequency relating to the user datum;
   determining a time period to fulfill the frequency requirement; and
   generating the device scheme as a function of the scan frequency and time period.

7. The system of claim 1, wherein generating the device scheme further comprises:
   generating a first device scheme as a function of a first scan frequency relating to a first signal profile;
   identifying a second scan frequency as a function of a user profile and first signal profile; and
   generating a second device scheme as a function of the user profile and second scan frequency.

8. The system of claim 1, wherein generating the device scheme further comprises:
   generating a first device scheme as a function of a first scan frequency relating to a first signal profile;
   identifying a second scan frequency as a function of a second signal profile; and
   generating a second device scheme as a function of the second scan frequency relating to the second signal profile.

9. The system of claim 1, wherein programming the monitoring device further comprises:
   obtaining a second device scheme;
   identifying, on the monitoring device, a first device scheme;
   comparing the first device scheme to the second device scheme; and
   programming the monitoring device as a function of the comparison.

10. A method for programming a monitoring device, the method comprising:
   obtaining by a computing device, from a monitoring device, a user datum of a plurality of user datum;
   calculating, by the computing device, a signal profile as a function of the user datum,
      wherein calculating the signal profile further comprises:
         receiving a signal training set, wherein the signal training set correlates a monitoring element and a vigor adjustment;
         configuring a signal machine-learning process as a function of the signal training set; and
         calculating the signal profile as a function of the signal machine learning process and the user datum;
   identifying, by the computing device, a scan frequency as a function of the signal profile,
      wherein identifying further comprises:
         receiving a frequency training set, wherein the frequency training set correlates at least a first vigor element and at least a first frequency requirement; and
         training a frequency machine-learning process as a function of the frequency training set; and
         identifying the scan frequency as a function of the signal profile and the frequency machine-learning process;
   generating, automatically, by the computing device, a device scheme as a function of the scan frequency; and
   programming, by the computing device, the monitoring device as a function of the device scheme.

11. The method of claim 1, wherein the signal profile further comprises a user vigor status.

12. The method of claim 10, wherein the signal profile comprises a vector enumeration relating to the user datum.

13. The method of claim 10, wherein the scan frequency comprises a number of scans required to monitor the user datum.

14. The method of claim 10, wherein the scan frequency further comprises a number of scans to at least monitor a user condition in a time period.

15. The method of claim 10, wherein generating the device scheme further comprises:

receiving a scan frequency relating to the user datum;

determining a time period to fulfill the frequency requirement; and generating the device scheme as a function of the scan frequency and time period.

16. The method of claim 10, wherein generating the device scheme further comprises:

generating a first device scheme as a function of a first scan frequency relating to a first signal profile;

identifying a second scan frequency as a function of a user profile and first signal profile; and generating a second device scheme as a function of the user profile and second scan frequency.

17. The method of claim 10, wherein generating the device scheme further comprises:

generating a first device scheme as a function of a first scan frequency relating to a first signal profile;

identifying a second scan frequency as a function of a second signal profile; and generating a second device scheme as a function of the second scan frequency relating to the second signal profile.

18. The method of claim 10, wherein programming the monitoring device further comprises:

obtaining a second device scheme;

identifying, on the monitoring device, a first device scheme;

comparing the first device scheme to the second device scheme; and programming the monitoring device as a function of the comparison.

* * * * *